United States Patent [19]

Schultz et al.

[11] Patent Number: 5,049,381
[45] Date of Patent: Sep. 17, 1991

[54] SKIN COLORING COMPOSITIONS CONTAINING INDOLES AND QUATERNARY AMMONIUM SALTS

[75] Inventors: Thomas M. Schultz, Highland Mills, N.Y.; George Serban, Ridgefield, Conn.; Alexander C. Chan, Mineola, N.Y.

[73] Assignee: Clairol Incorporated, New York, N.Y.

[21] Appl. No.: 440,536

[22] Filed: Nov. 22, 1989

[51] Int. Cl.$^5$ .................... A61K 7/021; A61K 31/40
[52] U.S. Cl. .................... 424/401; 424/59; 424/63; 514/415
[58] Field of Search .................... 424/401, 59, 63; 514/415

[56] References Cited

U.S. PATENT DOCUMENTS

| | | | |
|---|---|---|---|
| 4,390,341 | 6/1983 | Jacobs | 424/63 |
| 4,522,808 | 6/1985 | Jacquet et al. | 424/63 |
| 4,956,174 | 9/1990 | Lang et al. | 424/63 |
| 4,968,497 | 11/1990 | Wolfram et al. | 424/63 |

Primary Examiner—Thurman Page
Assistant Examiner—Amy Hulina
Attorney, Agent, or Firm—Sandra Nolan

[57] ABSTRACT

Compositions containing certain indoles and quaternary ammonium salts are useful for imparting a tan to skin without prolonged exposure to the sun.

18 Claims, 2 Drawing Sheets

SKIN COLORING COMPOSITIONS CONTAINING INDOLES AND QUATERNARY AMMONIUM SALTS

FIELD OF THE INVENTION

The invention relates to a cosmetic composition containing a quaternary ammonium halide and a selected indole to impart a tan coloration to the skin without the need for prolonged exposure to the sun.

BACKGROUND OF THE INVENTION

Suntanning is perceived to enhance personal appearance. As a result, many individuals actively seek a tan by exposing themselves to the sun. Such exposure, as is well known from human experience, often results in painful erythema or sunburn. It may also lead to premature aging of the skin, certain types of dermatological diseases and even skin cancer.

The art has, therefore, long sought chemical agents which will color the skin the characteristic bronze color of a natural tan, but will do so without exposure, or with minimum exposure to the sun. Such agents must be easily available, inexpensive, non-toxic, stable on storage and capable of imparting an even, long lasting coloration to the human skin.

One of the first agents found to be effective in generating a tan coloration to the human skin was dihydroxy acetone. Unfortunately, this material was found to be more reactive with some areas of the skin than others resulting in a speckled appearance after use, and frequently in an unpleasant yellow color on the skin.

Tanning is believed to be the result of melanin formation, a reaction which is triggered by the action of sunlight, principally the UV component of sunlight.

The actual mechanism by which melanin forms in the human body is not a part of this invention. It is believed that melanin is an oligomer containing several indole segments formed as a result of the cyclization and polymerization of dihydroxy phenylalanine (DOPA) caused by exposure to the sun.

Not surprisingly, the art has turned to indoles as of possible utility in coloring the skin. It has been shown that a number of indoles can impart color to the skin. European Patent Publication 0,239,896, incorporated by reference herein is one example of coloration by treatment with indoles.

The main problem associated with the use of indoles as tanning enhancers is that they bring about the color change very slowly. Thus, it takes several days after the application of the indole to the skin before the skin achieves an acceptable coloration. This period of time is longer than that needed for the skin to sunburn.

In order to obtain more rapid coloration the art has turned to the use of metallic salts such as copper or ferrous sulfates in combination with indole. Unfortunately, these salts cause such a rapid formation of melanin that only the outermost surface of the skin is colored and the resulting tan is too easily removed by ordinary washings. In addition, the resultant color is often grey rather than tan, contributing to an unpleasant yellow hue of the skin.

The need, then, is for an agent which will color the skin sufficiently in an acceptable period of time, i.e. before it has a chance to sunburn and to a depth which is adequate so that the resulting tan will not be eroded by ordinary day to day activities.

DETAILED DESCRIPTION OF THE INVENTION

Figure 1:
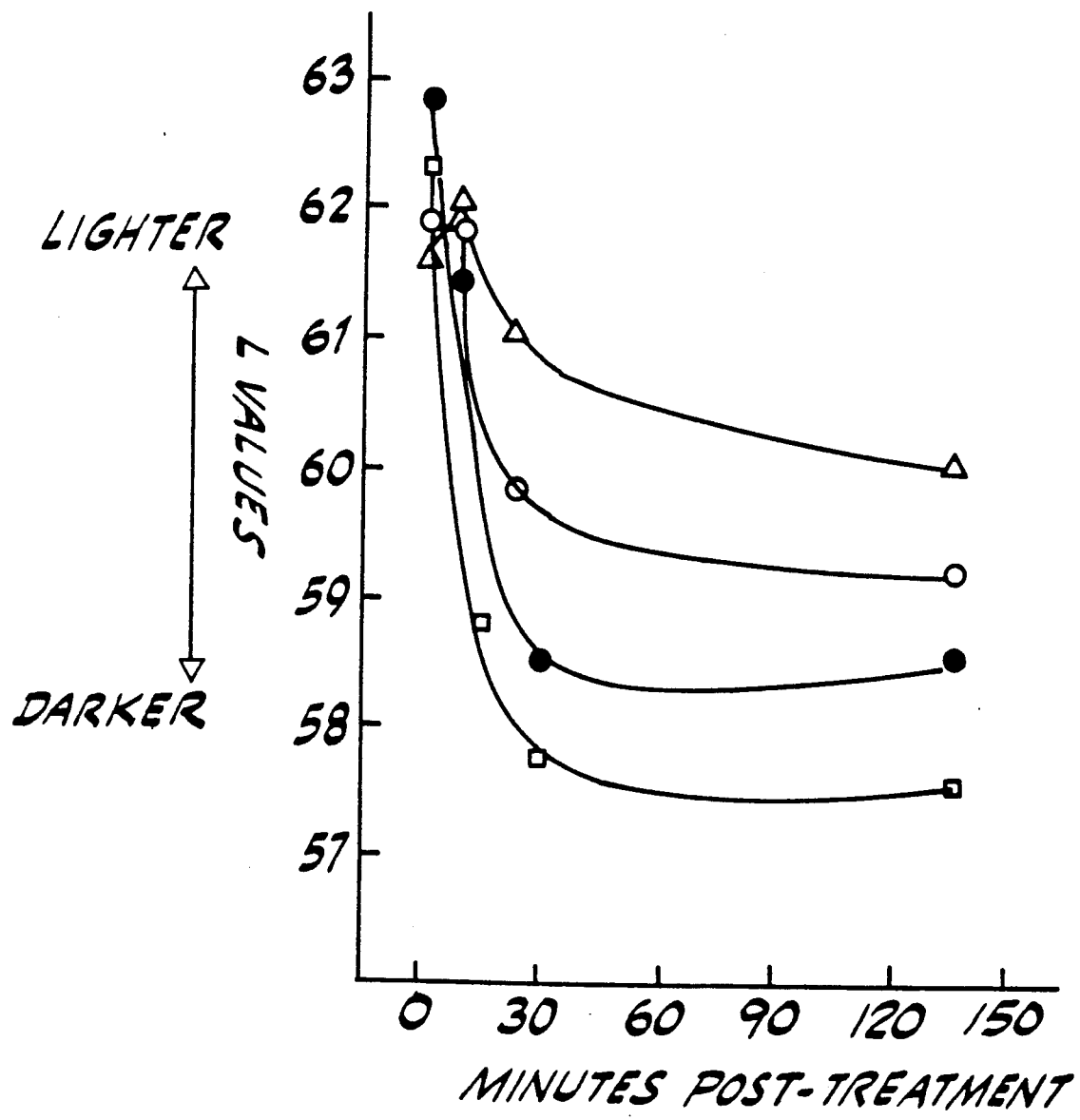
FIG. 1 and 2 show the results obtained in Examples 1 and 2 of this specification.

It has now been discovered that the formation of melanin to color the skin can be catalyzed by concurrent use of quaternary ammonium halides. The indole/quaternary salt combinations of the invention, when applied as a topical composition, will impart a deep, long lasting tan which will form on the skin to which it is applied within a satisfactory time period of about one half to about two hours without exposure to sunlight.

The invention therefore comprises skin coloring compositions containing a sufficient amount of an indole/quaternary ammonium salt mixture to be tinctorially effective for the formation of the characteristic bronze appearance of a tan.

The indoles and ammonium salts presently preferred for use in this invention are represented by the following formulas A and B respectively:

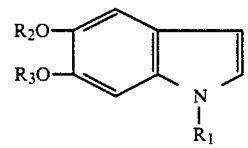 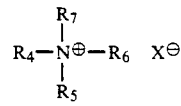

A          B wherein:

$R_1$ is hydrogen, $C_1$–$C_6$ alkyl, $C_1$–$C_6$ hydroxyalkyl or alkoxyalkyl containing a total of 2 to 6 carbon atoms;

$R_2$ and $R_3$, which may be the same or different, are hydrogen, $C_1$–$C_{12}$ alkyl, phenyl or $C_1$–$C_{18}$ acyl;

$R_4$, $R_5$, $R_6$ and $R_7$, which may be the same or different, are $C_1$–$C_{12}$ alkyl, $C_1$–$C_{12}$ hydroxyalkyl, $C_1$–$C_{12}$ alkoxyl phenyl, $C_1$–$C_{12}$ alkylphenyl, nitro substituted phenyl, amino substituted phenyl, nitro substituted $C_1$–$C_{12}$ alkylphenyl or amino substituted $C_1$–$C_{12}$ alkylphenyl;

and x is halogen.

The presently most preferred compounds for use in this invention are those in which the various R groups contain up to three carbon atoms, except that normally it is preferred that there be one long chain alkyl group ($C_{10}$–$C_{12}$) or alkylphenyl on the quaternary ammonium halide to limit water solubility so that it will resist removal by washing with water.

The most preferred indoles are 5,6-diacetoxy-N-methyl indole and 5,6-diacetoxyindole. The halide salt of choice is trimethyl benzyl ammonium iodide although others are also particularly effective. These include decyl trimethyl ammonium bromide, 2-(4-aminoanilino) ethyl trimethyl ammonium iodide, 2-(4-nitranilino) ethyl trimethyl ammonium iodide and bis-N,N-hydroxyethyl-N-methyl-N-dodecyl ammonium iodide. The compounds are preferred because they are readily available and because they are particularly effective in achieving the objectives of the invention.

A particular advantage of the composition of this invention compared to indoles alone is that the color produced in accordance with the invention is closer in appearance to a natural tan. As is well known to those skilled in the art, the use of indoles in low concentration on the skin produces a greyish tint. At high concentrations the color tends to be closer to black. However, the colors produced by the mixtures of this invention are the desirable golden and red browns that natural sunlight typically impart to skin.

The tanning compositions of this invention are preferably aqueous compositions. The term "aqueous composition" is used herein in its usual generic sense as embracing any water-containing composition useful for the present purposes. This includes true solutions of the selected compounds in an aqueous medium either alone or in conjunction with other materials, which are also dissolved or dispersed in the aqueous medium. The term "aqueous composition" also encompasses any mixture of the compounds used in the invention in the aqueous medium either alone or together with other ingredients. The various components may be colloidally dispersed in the medium or may merely be intimately mixed therein.

Moreover, the aqueous medium may comprise water or water and one or more additional or auxiliary solvents. Typical auxiliary solvents which may be used to enhance the solubility of the components include ethanol, carbitol, isopropanol, propylene glycol, ethylene glycol, diethylene glycol, diethylene glycol monoethyl ether, glycerine, etc.

The aqueous compositions of this invention can be prepared by conventional methods used in the art. Thus, they can be prepared by dissolving or suspending the components in the selected media with adequate mixing. Preparation may take place at ambient temperatures, i.e., 20° to 35° C., but solubility and rate of preparation can be enhanced utilizing elevated temperatures, for example 40° to 100° C.

Well known conventional additives usually employed in cosmetic compositions of this type such as thickeners, surface active agents, antioxidants, fragrances and chelating agents may be included in the compositions of the inventions. Such compositions are preferably liquid solutions but they may be in the form of emulsions, suspensions, lotions, or gels.

Surface active agents employed in the compositions of the invention can be anionic, nonionic or cationic. As examples of the various types of surface active agents there can be mentioned: higher alkylbenzene sulfonates; alkylnaphthalenesulfonates; sulfonated esters of alcohols and polybasic acids; taurates; fatty alcohol sulfates; sulfates of branched chain or secondary alcohols; alkyldimethylbenzylammonium chlorides, salts of fatty acids or fatty acid mixtures; N-oxyalkylated fatty acid alkanolamides, and the like. Illustrative of specific surfactants there can be mentioned: sodium lauryl sulfate; polyoxyethylene lauryl ester, myristyl sulfate, glyceryl monostearate, triethanolamine oleate, the sodium salt of palmitic methyl taurine, cetyl pyridinium chloride, lauryl sulfonate, myristyl sulfonate, lauric diethanolamide, polyoxyethylene stearate, ethoxylated oleyl diethanolamide, polyethylene glycol amides of hydrogenated tallow, stearyldimethyl benzyl ammonium chloride, dodecylbenzene sodium sulfonate, 2-amino-2-methyl propanol, the triethanolamine salt of p-dodecylbenzene sulfonate, the triethanolamine salt of p-dodecylbenzene sulfonate, nonylnaphthalene sodium sulfonate, dioctyl sodium sulfosuccinate, sodium N-methyl-N-oleoyl taurate, the oleic acid ester of sodium isothionate, sodium dodecyl sulfate, the sodium salt of 3-0-diethyl tridecanol-6-sulfate and the like. The quantity of surface active agent can vary over a wide range, such as from about 0.05% to 15% and preferably from about 0.10 to 5% by weight of the composition. Mixtures of various surfactants including mixtures of members of the various classes may be employed.

A thickening agent may also be incorporated in the compositions. These include, for example, such products as sodium alginate or gum arabic, or cellulose derivatives, such as methylcellulose, e.g. Methocel 60HG, or the sodium salt of carboxy-methylcellulose, or hydroxyethylcellulose, e.g. Cellosize QP-40 or acrylic polymers, such as polyacrylic acid sodium salt, or inorganic thickeners, such as bentonite. The quantity of this thickening agent can also vary over a wide range, even as high as 20%. Ordinarily it will range from about 0.5 to 5% by weight of the composition. The viscosity of the composition may vary from about 1 cps to about 100,000 cps. For a typical lotion formulation, composition viscosity is between about 100 cps to about 10,000 cps. Mixtures of these viscosity enhancing agents are operable.

It may also be useful to incorporate at least one antioxidant. A variety of antioxidants are known in the art which are useful for this purpose. Among these, mention may be made of the inorganic sulfites, e.g. sodium sulfite, thioglycollic acid and other mercaptans, butylated hydroxytoluene, sodium dithionite, various forms of ascorbic acid and its derivatives, e.g., sodium ascorbate, erythorbic acid, ascorbyl palmitate, ascorbyl laurate, etc. The quantity of antioxidant, when used can vary appreciably. In general, it may be up to about 5% by weight typically 0.001 to 5% preferably 0.01 to 1%.

The concentration of the selected indole and ammonium salts in the compositions of this invention may vary over a wide range depending principally on the intensity of the color change desired. Other factors readily evaluated by those skilled in the art will also be taken into consideration including, for example, the rate and degree of color change required.

Typically, the amount of indole or mixture of indoles in the cosmetic compositions will be from about 0.01% to 10% based on the total weight of the composition. On the same basis, the amount of ammonium salt or salt mixture is normally from about 0.001% to 1.00%.

The compositions of the invention may be packaged using conventional techniques appropriate to the composition type, e.g. liquid solutions or suspensions, gels, creams, ointments, etc. Liquid compositions are especially suitable for aerosol packaging in which the composition is packaged under pressure with a propellant such as a compressed gas or a liquified hydrocarbon or halogenated hydrocarbon such as butane or trichlorofluoromethane. The composition exits the container under pressure through a metering valve which may be especially designed to spread the skin coloring composition evenly over the skin surface to be treated.

In the method of the invention, the desired tanning is imparted to the skin by topical application of the selected composition by manually spreading on the area where the tan is desired, or by spraying or other equivalent means.

While the use of only one treatment with the composition is sufficient to cause some tanning—especially when sunlight is also contacted with the skin—the use of up to 6 or more applications is contemplated. Thus skin can be treated with the compositions of the invention from about 1 to 20 times, with optional exposure to sunlight.

The following examples are given by way of illustration only and should not be considered as limitations of the invention.

In the examples, color formation (tan) was measured using the Hunter Tristimulus Colorimeter. With this instrument, light/dark is represented as "L" value (decreasing value is darker) and the shade or hue by the "a" and "b" values. These values are arbitrarily selected so that +a is red, −a is green, +b is yellow and −b is blue. Thus, a gray or black color will have "a" and "b" values close to zero. A typical tan color will have strongly positive "a" and "b" values representing the reddish and yellowish brown color of a desirable tan shade.

EXAMPLE 1

The advantage of using an indole in combination with a quaternary ammonium halide is illustrated in FIG. 1. In this experiment, test sites on guinea pig skin were pretreated with 0.001% solutions of benzyltri-methyl ammonium iodide, copper sulfate or ferrous sulfate. Control areas received normal saline solutions. After 10 minutes the sites were rinsed with tap water and padded dry. The pretreated areas were then treated with the test indole, in this case 1% N-methyldiacetoxyindole in a 35% ethanol-water mixture. The figure shows that all treatments produced some degree of tanning as evidenced by the decrease in the "L" values. The sites pretreated with saline showed the least tan and they tended to develop an unnatural grey hue. On the other hand sites pretreated with $Cu^{++}$ or $Fe^{++}$ became darkest but they had a greenish appearance. Only the sites pretreated with the quaternary ammonium halide became sufficiently tanned and at the same time they produced a cosmetically pleasing appearance similar to a natural tan. The qualitative changes associated with the skin darkening observed in this experiment are shown with FIG. 1 in the form of "a" and "b" values. With no catalyst, and with the Cu and Fe salts the red hues of the skin are reduced ("a" value), while with the quaternary ammonium iodide the "a" value is significantly increased contributing to a more bronzed look—which is regarded as a desirable color. With the metal catalysts, the "b" value is strongly increased resulting in a significant, unpleasant yellowing of the skin hue. Overall the areas treated with the ammonium iodide were a much more natural tan color than those treated with no catalyst, or a metal salt catalyst.

5,6-Diacetoxyindole was substituted for the N-methyl derivative and similar results were obtained. Other halides found to be effective were decyl-trimethyl ammonium bromide, 2-(4-aminoanilino)ethyl-trimethyl ammonium iodide, 2-(4-nitroanilino)ethyl-trimethyl ammonium iodide, and bis-N,N-hydroxyethyl-N-methyl-N-dodecyl ammonium iodide.

EXAMPLE 2

Figure 2:
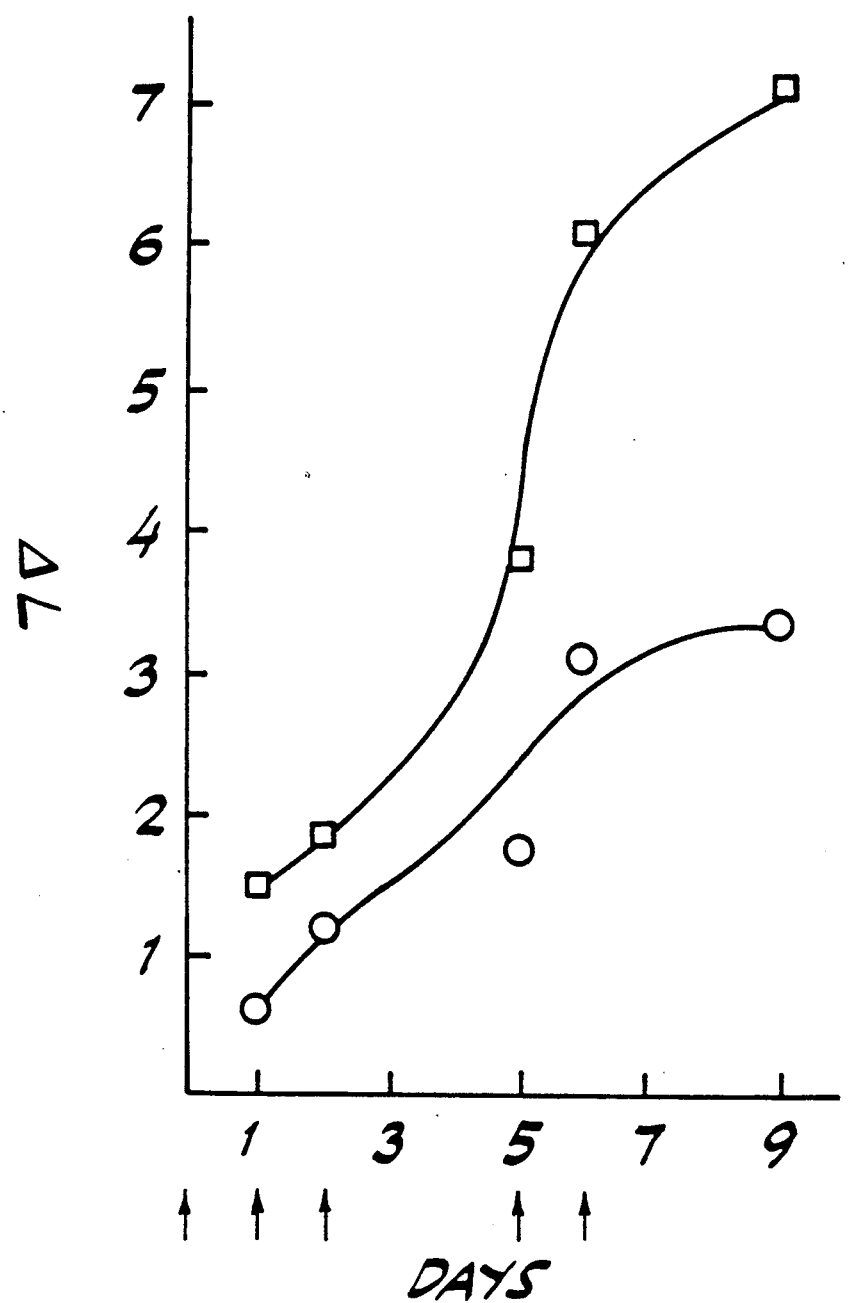

FIG. 2 further illustrates the advantage of using the quaternary ammonium halide as a catalyst. In this experiment the treatment was done with a mixture of N-methyldiacetoxyindole 0.1%) and benzyl trimethyl ammonium iodide (0.001%) in 25% ethanol water. The application was done by dispensing a small volume of the solution on the center of a delineated area of guinea pig skin. The solution was then spread out evenly. The experiment shows that repeated applications over a period of several days results in the build up of a strong tan. Prior to recording the "L" values and treatment renewal, the sites were thoroughly washed with soap and water. Thus, the "L" values shown in FIG. 2 are a reflection of substantive tanning, i.e. wash resistant. This is an important attribute since this characteristic enables bathing without loss of protection. The finding indicates that the mixture has optimal diffusional properties as well as reactivity. The number of applications required to attain an acceptable tan will depend on the concentrations of indole and quaternary ammonium halide on one hand and the desired intensity of tan on the other.

EXAMPLE 3

One of the general problems relating to the use of indoles as tanning agents is their relative lack of oxidative stability. Experiments were conducted to determine whether antioxidants, which would function as stabilizers, would affect the ability of an indole-quaternary halide mixture to produce tanning. For N-methyldiacetoxyindole (160 mg), benzyltrimethylammonium iodide (0.05 mg) and the antioxidant sodium ascorbate (40 mg) were dissolved in a commercially available skin cleansing lotion (water-glycerine base with octyl maleate and myristate as solubilizers). The experimental protocol was the same as that of Example 2. The results achieved showed that the composition was stable for a prolonged period of time at ambient temperature but it still produced tanning when applied to skin. Most likely due to the charged nature of the antioxidant, once applied to the skin it remains on the surface while the indole-quaternary ammonium halide diffuses inwards where it becomes free to undergo reaction to form a substantive tan.

Other antioxidants which functioned similarly are sodium sulfite, ethythorbic acid, thioglycollic acid and other mercaptans.

What is claimed is:

1. A skin coloring composition useful for imparting a tan appearance to the skin comprising a cosmetically acceptable carrier together with a tinctorially effective amount of a mixture of compounds represented by the following formulas A and B:

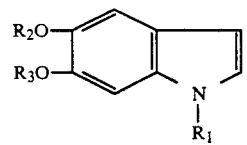
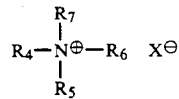

A           B wherein:
$R_1$ is hydrogen, $C_1$–$C_6$ alkyl, $C_1$–$C_6$ hydroxyalkyl or alkoxyalkyl containing a total of 2 to 6 carbon atoms;
$R_2$ and $R_3$, which may be the same or different, are hydrogen, $C_1$–$C_{12}$ alkyl, phenyl or $C_1$–$C_{18}$ acyl;
$R_4$, $R_5$, $R_6$ and $R_7$, which may be the same or different, are $C_1$–$C_{12}$ alkyl, $C_1$–$C_{12}$ hydroxyalkyl, $C_1$–$C_{12}$ alkoxyl phenyl, $C_1$–$C_{12}$ alkylphenyl, nitro substituted phenyl amino substituted phenyl, nitro substituted $C_1$–$C_{12}$ alkylphenyl or amino substituted $C_1$–$C_{12}$ alkylphenyl;
and x is halogen.

2. A composition of claim 1 containing, based on the total weight of the composition, from 0.01% to 10% of a compound of formula A, and from 0.001% to 1.00% of a compound of formula B.

3. A composition of claim 1 wherein the compound of formula A is selected from the group consisting of 5,6-diacetoxy-N-methyl indole, 5,6-diacetoxyindole and mixtures thereof and the compound of formula B is selected from the group consisting of decyl trimethyl ammonium bromide, 2-(4-aminoanilino) ethyl trimethyl ammonium iodide, 2-(4-nitroanilino) ethyl trimethyl ammonium iodide and bis-N,N-hydroxyethyl-N-methyl-N-dodecyl ammonium iodide, and mixtures thereof.

4. A composition of claim 1 wherein the compound of formula A is 5,6-diacetoxy-N-methyl indole and the compound of formula B is a benzyltrimethyl ammonium halide.

5. A composition of claim 4 wherein the halide is an iodide.

6. A composition of claim 2 wherein the compound of formula A is 5,6-diacetoxy-N-methyl indole and the compound of formula B is a benzyltrimethyl ammonium halide.

7. A composition of claim 6 wherein the halide is an iodide.

8. A composition of claim 1 wherein the compound of formula A is 5,6-diacetoxyindole and the compound of formula B is a benzyl trimethyl ammonium halide.

9. A composition of claim 8 wherein the halide is an iodide.

10. A composition of claim 2 wherein the compound of formula A is 5,6-diacetoxyindole and the compound of formula B is a benzyl trimethyl ammonium halide.

11. A composition of claim 10 wherein the compound of formula A is 5,6-diacetoxyindole and the compound of formula B is a benzyl trimethyl ammonium halide.

12. A process for coloring skin comprising topical application to the skin of a composition of claim 1.

13. A process for coloring skin comprising topical application to the skin of a composition of claim 2.

14. A process for coloring skin comprising topical application to the skin of a composition of claim 3.

15. A process for coloring skin comprising topical application to the skin of a composition of claim 6.

16. A process for coloring skin comprising topical application to the skin of a composition of claim 7.

17. A process for coloring skin comprising topical application to the skin of a composition of claim 10.

18. A process for coloring skin comprising topical application to the skin of a composition of claim 11.

* * * * *